United States Patent
Krakers et al.

(10) Patent No.: US 7,815,877 B2
(45) Date of Patent: Oct. 19, 2010

(54) STERILIZING DEVICE FOR STERILIZING CLOSURES

(75) Inventors: Bernardus Antonius Johannes Krakers, Uitgeest (NL); Arie Zalm, Enkhuizen (NL)

(73) Assignee: Stork Food & Dairy Systems, B.V., Amsterdam (NL)

( * ) Notice: Subject to any disclaimer, the term of this patent is extended or adjusted under 35 U.S.C. 154(b) by 1066 days.

(21) Appl. No.: 11/013,205

(22) Filed: Dec. 15, 2004

(65) Prior Publication Data

US 2005/0169796 A1 Aug. 4, 2005

(30) Foreign Application Priority Data

Dec. 18, 2003 (NL) .................................. 1025060
Mar. 30, 2004 (NL) .................................. 1025847

(51) Int. Cl.
*A61L 2/00* (2006.01)
*A61L 9/00* (2006.01)
*A61L 2/18* (2006.01)

(52) U.S. Cl. ..................................... 422/302; 422/304
(58) Field of Classification Search .................. 53/476, 53/285, 426; 221/282; 422/302, 304
See application file for complete search history.

(56) References Cited

U.S. PATENT DOCUMENTS

| 3,455,644 | A | | 7/1969 | Arber |
| 3,905,317 | A | * | 9/1975 | Pacilio ........................ 215/200 |
| 4,167,797 | A | * | 9/1979 | Wilde et al. .................... 15/302 |
| 4,304,611 | A | * | 12/1981 | Ellis ............................ 134/23 |
| 6,536,188 | B1 | | 3/2003 | Taggart |
| 2003/0159754 | A1 | * | 8/2003 | Bausch ........................ 141/168 |

FOREIGN PATENT DOCUMENTS

| DE | 30 09 202 A1 | 9/1981 |
| DE | 101 45 102 A1 | 10/2003 |
| JP | 04 044938 A | 2/1992 |
| JP | 06293319 A * | 10/1994 |
| JP | 10085311 A * | 4/1998 |
| JP | 11 139416 A | 5/1999 |
| WO | WO 00/27440 | 5/2000 |
| WO | WO 00/46142 | 8/2000 |
| WO | WO 2004/018298 | 3/2004 |

OTHER PUBLICATIONS

English Translation of Japanese Patent No. JP410085311A—Hishida, Masanori; Transporting Equipmen t, and apparatus for sterilization of cap utilizing the same; Apr. 1998.*
English Translation of Japanese Patent No. JP406293319A—Takagi, Masatoshi; Cap Sterilizer for Container; Oct. 1994.*

* cited by examiner

*Primary Examiner*—Sean E Conley
*Assistant Examiner*—Kevin C Joyner
(74) *Attorney, Agent, or Firm*—Hoffman & Baron, LLP

(57) ABSTRACT

The invention relates to a sterilizing device (10) for sterilizing closures (16), such as lids and caps for containers, such as bottles and jars, which device comprises a housing (12), provided with a closure entry (14) for supplying closures, a closure exit (18) for discharging sterilized closures from the device, a sterilizing-agent feed (21) for feeding sterilizing agent into the device and a discharge (28; 30) for discharging used sterilizing agent, as well as pass-through means (20) for passing closures (16) through the housing (12), the pass-through means (20) comprising a non-rectilinear pass-through path (58) in the plane parallel to the main plane of the closures. A sterilizing method is also described.

16 Claims, 2 Drawing Sheets

STERILIZING DEVICE FOR STERILIZING CLOSURES

CROSS-REFERENCE TO RELATED APPLICATIONS

This application, claims the benefit of Netherlands Application Nos. NL 1025847, filed Mar. 30, 2004 and NL 1025060, filed Dec. 18, 2003, the contents of which are incorporated by reference herein.

FIELD OF THE INVENTION

The invention relates to a sterilizing device for sterilizing closures, as is used in aseptic filling devices.

BACKGROUND OF THE INVENTION

In aseptic filling devices, containers, such as bottles, jars, cans and the like, are filled with free-flowing products, in particular flowable food products with a limited shelf life, under aseptic conditions. In a device of this type, the bottles are first of all sterilized, then filled and closed with a closure, such as a thin Al foil, a metal lid or a plastic cap. The closure has also been sterilized.

An aseptic filling device of this type in which the closures are conveyed through the sterilizing device and filling device with the aid of a chain mechanism, for example from the entry position for the closures through a sterilizing bath to a position where the closures are transferred and fitted to the containers, which have in the meantime been filled, is known in the art. However, chain mechanisms in aseptic filling devices and auxiliary devices thereof are themselves difficult to clean and sterilize, and therefore inspection services and other licensing authorities view chain mechanisms of this type with considerable distrust. In addition, wear is inevitable, resulting in dust and coarser particles. This leads to the formation of fat, grease and other dirt, which exacerbates the abovementioned cleaning and sterilization problem. The reliability also leaves something to be desired on account of the presence of mechanically driven components in the chain mechanism, which entails the risk of the filling device having to be shut down altogether.

SUMMARY OF THE INVENTION

It is an object of the present invention to avoid the abovementioned drawbacks and to provide solutions to the above problem.

To this end, the invention provides a sterilizing device for sterilizing closures, such as lids and caps for containers, such as bottles and jars, which device comprises a housing, pass-through means for passing closures through the housing under the influence of the force of gravity, which housing is provided with a closure entry for supplying closures at the top of the pass-through means, a closure exit for discharging sterilized closures from the device at the bottom of the pass-through means, a sterilizing-agent feed for feeding sterilizing agent into the device and a discharge for discharging used sterilizing agent, the pass-through means comprising a non-rectilinear pass-through path in the plane parallel to the main plane of the closures.

In the sterilizing device according to the invention, the closures, under the influence of the force of gravity, follow a non-rectilinear pass-through path which is delimited by the pass-through means within the housing. Since chains or other mechanical drives are not used to displace the closures, the associated problems of wear and contamination do not arise.

In the context of the present application, the term main plane of a closure is to be understood as meaning the plane parallel to the flat top side, which contrasts, for example, with the plane of a bent-over rim of a lid or cap.

At or in the vicinity of the top side of the housing, the closures are introduced into the pass-through means via the closure entry and then moved downwards along the pass-through path. During this movement, the closures are sterilized on all sides by being exposed to a sterilizing agent, preferably hydrogen peroxide vapour. The pass-through means—sometimes also referred to below as a chute—do not delimit a completely straight pass-through path, but rather at least a portion of the pass-through path, in the active zone of the sterilizing device, follows a non-rectilinear two-dimensional sliding or falling path portion in the plane parallel to the main plane of the closure, within which the closures move under their own weight. The pass-through means guide the closures from the closure entry through the active sterilizing zone to the closure exit. The pass-through means may be positioned vertically in the device according to the invention. They are advantageously at a small angle of, for example, 3° with respect to a vertical axis, so that a fluctuating part of the back side of the closures is always in contact with the pass-through means in the pass-through path. The result of this is that only one side of the closure will come into contact with the chute, but the contact point is not always the same on account of the non-rectilinear path portion, and consequently the entire lid is exposed to the sterilizing agent. Complete exposure is boosted further by the fact that the friction between a closure and the chute will generally effect a certain rotation of the closure, and consequently successive closures will also not always come to bear against one another at the same positions. The result of this is that there is no fixed point of contact between a closure and the chute, on the one hand, and between successive closures, on the other hand. An optional pull lip may limit rotation to some extent but does not lead to a fixed contact point and does not prevent the entire surface of a closure from being exposed to the sterilizing agent.

The pass-through means are shaped in such a manner that, at least over a certain portion thereof in the active zone of the device, the points of contact are not positions which are fixed with respect to one another, but rather vary along the pass-through path. This can be achieved, for example, by providing the pass-through means with projections which cause a forced rotation or displacement of the closures with respect to one another and with respect to the pass-through means.

According to a preferred embodiment, the pass-through path comprises a wavy path. By providing the pass-through path with a wavy pattern with gradual transitions between wave peaks and valleys, the movement of the closures in the pass-through means is made reasonably even and there is little risk of blockages or stoppages, as could occur with sharp transitions or angles. To facilitate the introduction and removal and the control thereof, it is possible to provide a generally short straight path at the entry and exit sides of the pass-through means. The movement of closures during sterilization with respect to one another can also be obtained by providing one or more projections in straight pass-through means, with which projections the closures come into contact, resulting in the formation of a non-rectilinear pass-through path, so that the position of the closures with respect to one another changes and contact between successive closures is not constant. Therefore, an embodiment of the pass-through means of this type likewise has a non-rectilinear pass-through path in the active zone of the sterilizing device.

In a preferred embodiment, the pass-through means comprise box-section parts which interact with one another and have edge parts facing one another, which box-section parts are arranged so as to leave clear a narrow exit gap for sterilizing agent between the edge parts. In this embodiment, the chute advantageously comprises two mating box-section parts, of which the base, which runs parallel to the abovementioned main plane of the closures, is slightly larger than the maximum width or diameter of the closures. The ends of the box-section parts are provided with edge parts or flanges. The interacting box-section parts are disposed with the edge parts opposite one another, in such a manner that a narrow gap remains between them. For this purpose, it is possible for one or more spacers or stops to be provided on the edge parts. Via this narrow gap, sterilizing agent is discharged from the chute. The narrow gap is also of importance for pressure control, as will be explained in more detail below.

To enable the resistance of the narrow gap to be reduced, it is advantageously possible to provide an edge part of a box-section part with a section which extends obliquely away from that edge part of the other box-section part with which it interacts. As a result, the gap widens in the direction of the sterilizing agent flowing out of the pass-through means. With relatively narrow edge parts, an inclination of this type will advantageously be arranged on those portions where the wavy passage of the path and the like permits, i.e. between two peaks.

In a further preferred embodiment, the base of the box-section parts is provided with at least one feed opening for feeding sterilizing agent to the closures. The result of this embodiment is that the sterilizing agent, via the feed opening (s) in the base, is brought into virtually direct contact with both the top side (outer side) and the underside (inner side) of the closure. It is advantageous for a number of feed openings to be distributed over the length of the path of the conveying passage in the base of a box-section part. The sterilizing agent supplied will make a further contribution to the movement of the closures with respect to one another and with respect to the box-section parts, so that no fixed points of contact occur between them. To further boost this effect, it is preferable for the feed openings in the interacting box-section parts to be arranged offset with respect to one another, in such a manner that sterilizing agent is constantly blown onto a closure from all sides.

The sterilizing-agent feed advantageously comprises feed tubes which are arranged between the base of the box-section parts and the housing and have at least one discharge opening directed towards the base of a box-section part. More preferably, the discharge openings of the corresponding feed tube are in line with the feed openings in the base of a box-section part. With a view to maintaining the pressure, the dimensions of the discharge openings in the feed tubes are advantageously smaller than the feed openings in the base of the box-section parts. The relatively small discharge openings in the feed tubes produce a resistance to outgoing flow which contributes to distributing the vapour of the sterilizing agent across all the openings. From a practical perspective, the feed openings are larger than the abovementioned discharge openings in order to compensate for any alignment errors in the small discharge openings.

It is advantageous for the sterilizing-agent feed to comprise distribution means for feeding sterilizing agent to both ends of the feed tubes.

In a further preferred embodiment of the sterilizing-agent feed, the latter comprises an entry opening, which is in communication with a distribution space that in turn is in communication with one or more annular feed channels and a (central) pass-through channel. In this embodiment, the quantity of sterilizing agent which flows in via the entry opening is divided into two or more streams. The first part flows through the annular feed channels. The second part flows through the internally positioned pass-through channel, which opens out into a second distribution space that is in communication with the other end of the feed channels. The feed tube having at least one discharge opening, which may be the outermost annular feed channel that adjoins the pass-through means, is therefore supplied with sterilizing agent from both ends, and in this way a uniform distribution of sterilizing agent is achieved in the active zone via the discharge openings.

The device according to the invention will usually comprise pass-through means having a plurality of non-rectilinear pass-through paths as defined above, in which case each pass-through path may if desired be provided with a dedicated closure entry and exit. During operation, the sterilizing device according to the invention is held under a slight vacuum. Since an active zone comprising sterilizing agent is present in the sterilizing device according to the invention, any inward leakage of non-sterile ambient air does not cause a problem. However, in view of current safety regulations, this prevents sterilizing agent from leaking out of the device to the working environment. The sterilizing agent is preferably applied to the closures in vapour form, for example hydrogen peroxide in sterile air, without condensation occurring.

To preheat the device and maintain the temperature in order to prevent condensation of sterilizing agent, the housing is advantageously also provided with a carrier-gas feed, which is located in the centre as seen in the direction in which the closures are conveyed, for feeding a carrier gas to the space between the pass-through means and the housing, the discharge for sterilizing agent comprising discharges in the vicinity of the top side and the underside of the housing. In this embodiment of the device according to the invention, heated carrier gas, in particular sterile air, is introduced into the space between the housing and the pass-through means, where it is distributed both upwards and downwards and can thereby reach all corners. In this space, this sterile air is mixed with the sterilizing-agent vapour originating from the pass-through means. The mixture formed is discharged from the housing at the top side and the underside.

If desired, additional control gas, likewise sterile air, can be introduced in the vicinity of the underside of the pass-through means in order to aid the transfer of the sterilized closures to the filling machine. This control gas can if desired also provide a certain subsequent drying effect.

The closure entry is preferably designed as an entry lock, in such a manner that a controlled number of, for example one or two, closures from a series of closures is in each case admitted to the device. In a structurally simple embodiment, an entry lock of this type comprises two pins which can be moved into the feed path of the closures. The movable pins are controlled in such a way that it is impossible for both pins to be retracted simultaneously, which could lead to unimpeded passage of closures. It is advantageous for the closure exit to be designed in the same way.

It is preferable for the closure entry and exit to be controlled with the aid of a control device on the basis of signals originating from proximity sensors for detecting the presence or absence of closures.

The sterilizing device according to the invention can be used in systems for the aseptic packaging of sterile food products in containers, such as bottles, jars, cans, tubs, etc., which, as well as the associated closures, have been presterilized. Packaged food products can be classified as high-acidity products (pH≦4.5) or low-acidity products (pH≧4.5). The packaging requirements for low-acidity products are generally higher compared to high-acidity products, since in the case of the latter the acidic medium contributes to the shelf life of the product by inhibiting the growth of bacteria. The sterilizing device according to the invention is suitable for use in the aseptic packaging of low-acidity food products and complies with the US standard for aseptic packaging laid down by the FDA. In the present description, the term "aseptic" therefore also refers to this standard. Obviously, it will be understood that the device according to the invention also complies with less strict legislation. The present invention provides the greatest advantages in the sterilizing of closures under aseptic conditions, in which case the aseptically sterilized closures are fitted to aseptically sterilized containers after the latter have been filled with food products which have been preserved under aseptic conditions.

The invention also provides a method for sterilizing closures, such as lids and caps for containers, such as bottles and jars, comprising an exposure step of exposing the closures to a sterilizing agent, with the position of successive closures with respect to one another being altered during at least part of the exposure step. The method according to the invention, in particular in a sterilizing device without mechanical conveyor means for the closures, ensures that all parts of a closure are exposed to the sterilizing agent without any fixed points of contact occurring between individual closures or between the closures and the pass-through means used, which fixed points of contact are not exposed to sterilizing agent.

The method according to the invention can be carried out, for example, in a sterilizing device according to the invention, in which case the successive closures come into contact with one another. In this embodiment, the successive closures are constantly in contact with one another but not at the same points or surfaces of contact.

As has already been explained in connection with the device according to the invention, the exposure step is preferably carried out under aseptic conditions.

The change in the position of successive closures with respect to one another advantageously comprises at least one rotary movement of the closures.

The method according to the invention can advantageously be implemented by imparting a forced movement to the closures with respect to one another during sterilization, as is achieved in the device according to the invention by pass-through means having a non-rectilinear path portion in the active zone.

BRIEF DESCRIPTION OF THE DRAWINGS

The invention will be explained in more detail below with reference to the appended drawing, in which.

DETAILED DESCRIPTION OF PREFERRED EMBODIMENTS

Figure 1:
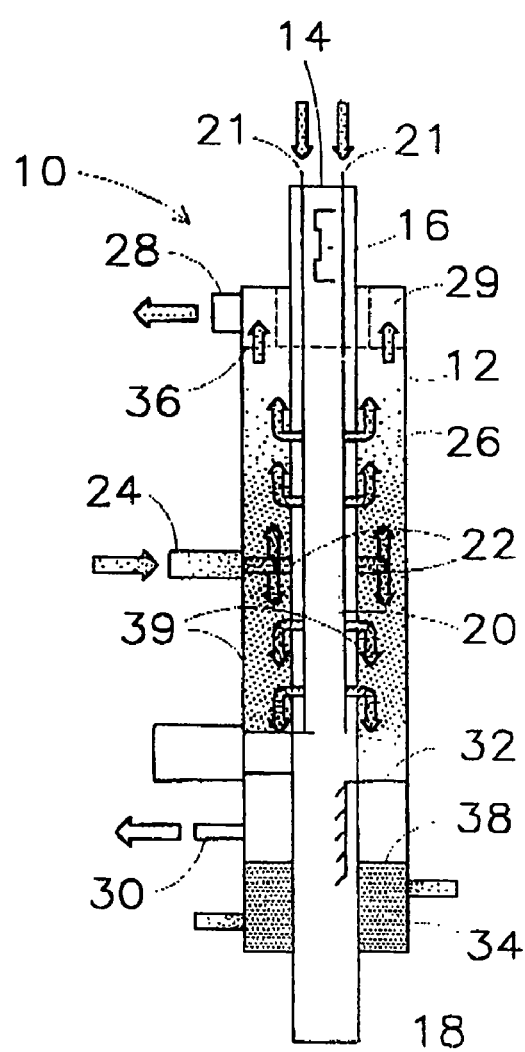
FIG. 1 shows a diagrammatic cross section through an embodiment of a sterilizing device according to the invention.
Figure 5:
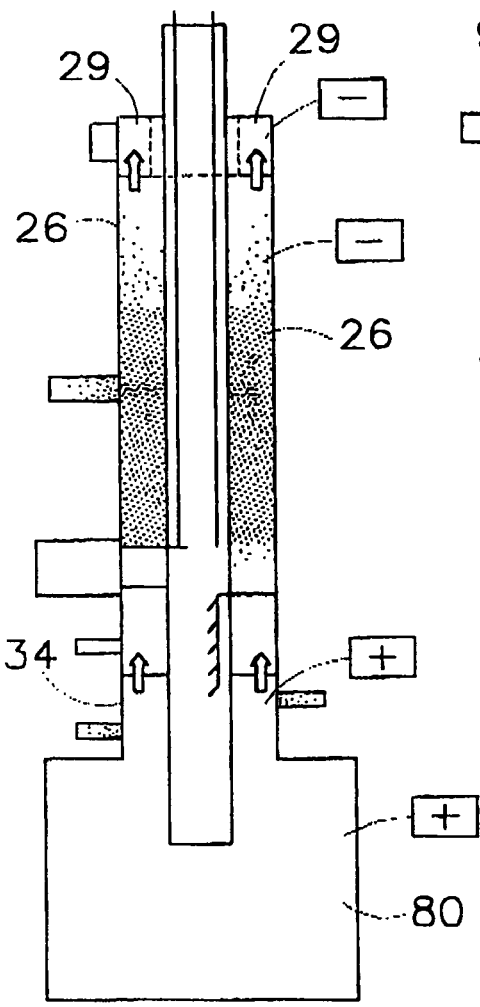
FIG. 5 shows the pressure conditions in an embodiment of a sterilizing device.

FIG. 1 diagrammatically depicts a sterilizing device 10 for sterilizing closures according to the invention. The device 10 comprises a vertically disposed, elongate housing 12 having a central, top entry 14 for the entry of closures 16, one of which is diagrammatically depicted in the form of a cross section of a cap, and having a central, bottom exit 18 for the exit of closures after sterilization. Pass-through means 20 in the form of a chute are located in the housing 12 between entry 14 and exit 18. Feed tubes 21 for supplying sterilizing agent, such as hydrogen peroxide, are arranged along the chute 20. The feed tubes are provided with double exit openings 22 (cf. FIG. 2). The direction of flow of the sterilizing agent is indicated by arrows. The housing 12 also comprises an entry 24, located approximately halfway up the device, for the introduction of carrier gas, such as sterile air, to prevent condensation of the sterilizing agent by heating the device. Between the housing 12 and the chute 20 there is a chamber 26, where the sterilizing agent which flows out of the chute 20 is mixed with the carrier gas and in this way exposes the interior of the entire device to the sterilizing agent. The carrier gas, mixed with the sterilizing agent, is discharged via dischargers 28 (for air discharge chamber 29) and 30 provided at the ends of the housing 12. If desired, an auxiliary gas, such as sterile air, can be introduced at 32 in order to (further) dry the sterilized closures if appropriate and to discharge them from the device. The bottom portion 34—also referred to as the drying section or chute cover—forms part of the aseptic zone of the filling machine (FIG. 5). The active sterilizing zone of the device is therefore limited by an air inlet plate 36 towards the air discharge chamber 29, the base 38 and the side walls 39 of the housing 12.

Figure 2:
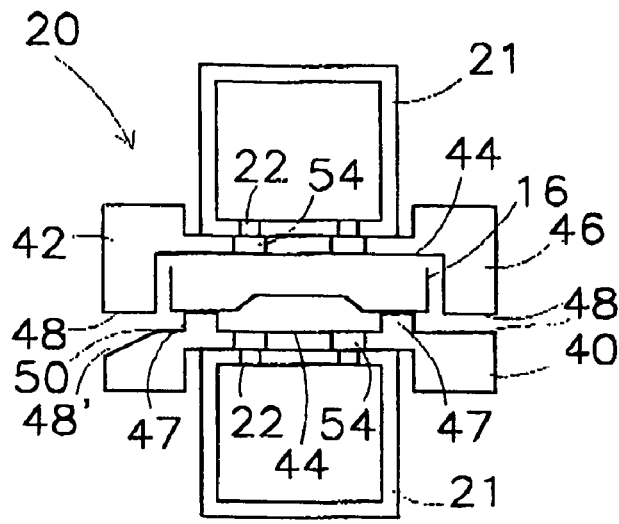
FIG. 2 shows a diagrammatic cross section through an embodiment of pass-through means composed of box-section parts for a sterilizing device according to the invention.

FIG. 2 shows a diagrammatic cross section through an embodiment of pass-through means 20. The pass-through means 20 are composed of two box-section parts 40 and 42 arranged opposite one another. Box-section part 42 comprises a substantially U-shaped profiled section comprising a base 44 and upright limbs 46. Box-section part 40 likewise comprises a base 44, which is provided with two slide ribs 47 against which a closure 16 bears. Box-section parts 40 and 42 face one another. The base 44 runs parallel to the main plane of the closure 16. The limbs 46 of box-section part 42 are provided at their end with an outwardly extending edge part 48. Box-section part 40 is also provided with edge parts 48 of this type. Between interacting edge parts 48 there is a narrow gap 50, through which sterilizing agent can flow out. This sterilizing agent is supplied via feed tubes 21 provided with a discharge opening 22 directed towards the corresponding box-section part via a corresponding opening 54 with a larger diameter than the discharge opening 22. The openings 22 and 54 in a box-section part and associated feed tube are designed to be slightly offset with respect to the corresponding openings in the opposite box-section part with associated feed tube. The first openings, as seen in the pass-through direction of the closures, are located directly at the entry to the sterile zone. In this way, the underside and top side of a closure 16 are immediately exposed to the sterilizing agent, followed by the side edges, on account of the shape of the conveyor path and forced flow. To lower the resistance of the gap 50, it is possible for an edge part $48^1$ of portion thereof to be turned towards the base 44, as indicated for box-section part 40. Cf. also FIG. 3.

Figure 3:
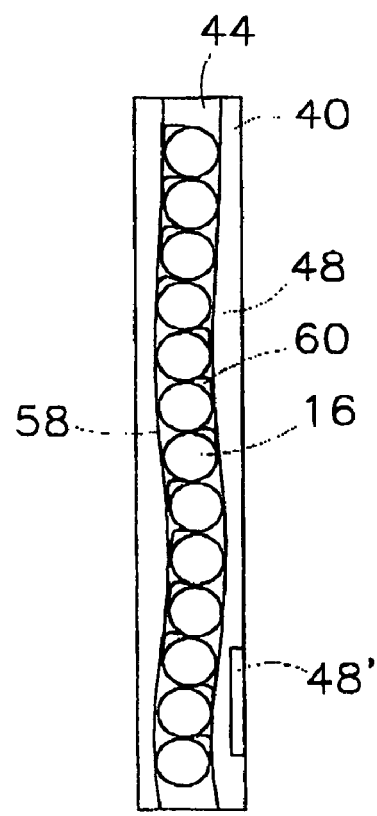
FIG. 3 shows a diagrammatic view of a box-section part with closures.

FIG. 3 shows an embodiment of a box-section part having a wavy pass-through path 58 for the closures 16 with pull lip 60. As a result of the force of gravity, the non-rectilinear path 58 and the flow of sterilizing agent, a closure does not have any constant points of contact over the pass-through path with the box-section parts or with other adjacent closures.

Figure 4:
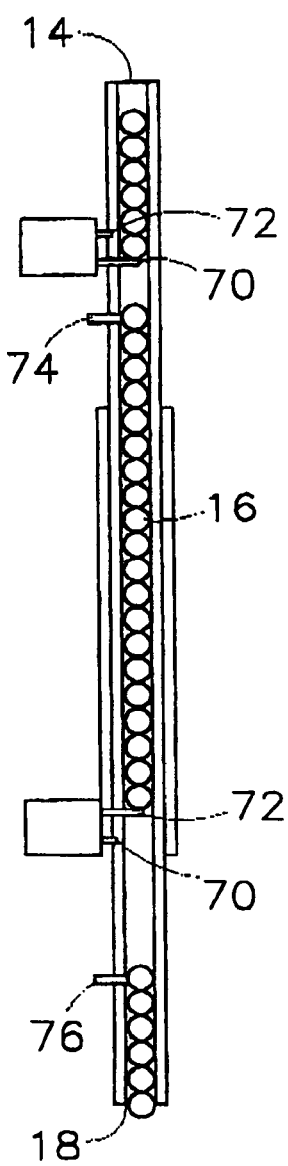
FIG. 4 shows an embodiment of a sterilizing device according to the invention with a diagrammatically depicted control of the closure entry and discharge.

FIG. 4 shows the entry 14 and exit 18 for closures 16, the path being shown as a straight path in order to simplify the illustration. The entry 14 and exit 18 each form a separately actuable lock, comprising two pneumatically driven pins 70 and 72. A sensor 74 detects the presence of closures in the pass-through path. The entry 14 is controlled on the basis of a signal originating therefrom. A sensor 76 detects the presence of closures in the connection to the filling machine (cf. also FIG. 5). The exit 18 is controlled on the basis of a signal originating from the sensor 76. This control is such that two pins can never be retracted simultaneously. The entry 14 is designed in such a manner that only one closure 16 is allowed to pass through per cycle. The exit 18 is designed to allow in each case two closures per cycle to pass through. Therefore, the cycle time of the latter is double the cycle time of the entry 14. Variations on this, such as 1:1, 2:2, etc., are, of course, also possible. The control is also designed in such a way that the same number of closures are introduced into the sterilizing device as are discharged.

FIG. 5 diagrammatically depicts a sterilizing device 10 according to the invention connected to a filling machine 80.

Within the air-discharge chamber 29, the pressure is "−−" (the pressure is presented in relative values). This generates a flow of air upwards into the chamber 26. In the active sterilizing zone, the pressure is "−", and in the drying section 34 the pressure is "+" (equal to the pressure in the aseptic zone of the filling machine 80), which results in a flow of air from the aseptic drying section 34 towards the active sterilizing zone. Since the pressure in the filling machine 80 is higher than the pressure in the sterilizing device 10 itself, it is possible to open the device 10 without interrupting the sterile conditions in the filling machine 80.

Figure 6:
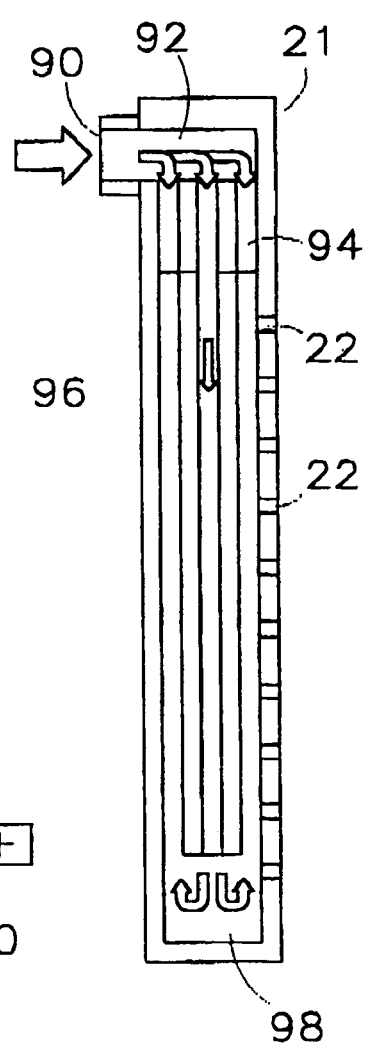
FIG. 6 shows a preferred embodiment of a sterilizing-agent feed.

FIG. 6 diagrammatically depicts a feed tube 21, which comprises an entry opening 90 for supplying sterilizing agent, providing access to a distribution space 92. An annular feed channel 94 and a central pass-through channel 96 are located in the feed tube 21. That part of the annular feed channel 94 which adjoins the pass-through means (not shown in FIG. 6) is provided with discharge openings 22 which are distributed over the length. The bottom ends of the annular channel 94 and central channel 96 open out into a second distribution space 98. The direction of flow and distribution of sterilizing agent are indicated by arrows.

What is claimed is:

1. Sterilizing device for sterilizing closures, such as lids and caps for containers, such as bottles and jars, which device comprises a housing, which housing is provided with a closure entry for supplying closures at the top of a pass-through means, a closure exit for discharging sterilized closures from the device at the bottom of the pass-through means, the pass-through means for passing closures through the housing under the influence of the force of gravity from said closure entry to said closure exit, a sterilizing-agent feed for feeding sterilizing agent into the device and a discharge for discharging used sterilizing agent, the pass-through means comprising a non-rectilinear pass-through path in the plane parallel to the main plane of the closures.

2. Sterilizing device according to claim 1, in which the pass-through path comprises a wavy path.

3. Sterilizing device according to claim 1, in which the pass-through means comprise box-section parts which interact with one another and have edge parts facing one another, which box-section parts are disposed so as to leave clear a narrow exit gap for sterilizing agent between the edge parts.

4. Sterilizing device according to claim 3, in which at least one edge part of a box-section part is provided with a section which extends obliquely away from that edge part of a box-section part which interacts with it.

5. Sterilizing device according to claim 3, in which the box-section parts comprises at least one feed opening for feeding sterilizing agent to the closures.

6. Sterilizing device according to claim 5, in which the feed openings in the interacting box-section parts are arranged offset with respect to one another.

7. Sterilizing device according to claim 1, in which the sterilizing-agent feed comprises feed tubes which are disposed between the base of the box-section parts and the housing and have at least one discharge opening directed towards the base of a box-section part.

8. Sterilizing device according to claim 7, in which the dimensions of the discharge openings of the feed tubes are smaller than the feed openings of the box-section parts.

9. Sterilizing device according to claim 7, wherein the sterilizing-agent feed comprises distribution means for feeding sterilizing agent to the ends of the feed tubes.

10. Sterilizing device according to claim 1, in which the housing is also provided with a carrier-gas feed, which is located in the centre as seen in the direction in which the closures are conveyed, for feeding a carrier gas to the space between the pass-through means and the housing, the discharge for sterilizing agent comprising discharges in the vicinity of the top side and the underside of the housing.

11. Sterilizing device according to claim 1, in which the closure entry comprises an entry lock.

12. Sterilizing device according to claim 11, in which the entry lock comprises two pins which can be moved into the feed path of closures.

13. Sterilizing device according to claim 1, in which the closure exit comprises an exit lock.

14. Sterilizing device according to claim 13, in which the exit lock comprises two pins which can be moved into the exit path of the closures.

15. Sterilizing device according to claim 1, which sterilizing device comprises a control device for controlling the closure entry and closure exit on the basis of signals originating from proximity sensors for detecting the presence of closures.

16. Device according to one claim 1, which is designed to sterilize closures under aseptic conditions.

* * * * *